United States Patent [19]

Nagashima et al.

[11] Patent Number: 5,371,269
[45] Date of Patent: Dec. 6, 1994

[54] METHOD FOR PRODUCTION OF α-L-ASPARTYL-L PHENYLALANINE METHYL ESTER HYDROCHLORIDE

[75] Inventors: Kazutaka Nagashima; Satoji Takahashi, both of Yokkaichi, Japan

[73] Assignee: Ajinomoto Co., Inc., Tokyo, Japan

[21] Appl. No.: 79,552

[22] Filed: Jun. 22, 1993

[30] Foreign Application Priority Data

Jun. 29, 1992 [JP] Japan ................................ 170654
Jul. 8, 1992 [JP] Japan ................................ 180837

[51] Int. Cl.$^5$ ......................................... C07C 229/34
[52] U.S. Cl. ..................................................... 560/41
[58] Field of Search ............... 560/40, 41, ; 562/450

[56] References Cited

U.S. PATENT DOCUMENTS 4,684,745 8/1987 Takemoto et al. ............... 560/41
4,803,300 2/1989 Hijiya et al. ....................... 562/450

OTHER PUBLICATIONS

Chemical abstracts, vol. 87, No. 17, Oct. 24, 1977, Masahiko Fujino, et al., "Aspartyl Dipeptide Esters", p. 800, AN 136 391g.
Chemical Abstracts, vol. 79, No. 11, Sep. 17, 1973, Yasuo Ariyoshi, et al., "Synthesis Of A Sweet Peptide, Alpha–L–Aspartyl–L–Phenylalanine Methyl Easter, Without The Use Of Protecting Groups", p. 484, AN 66 803b.
Chemical Abstracts, vol. 85, No. 1, Jul. 5, 1976, Noboru Uchiyama, et al., "Alpha–L–Aspartyl–L–Phenylalanine Lower Alkyl Esters", p. 492, AN 6056Z.
Chemical Abstracts, vol. 113, No. 15, Oct. 8, 1990, Yutaka Shiokawa, et al., "Manufacture Of Granular Alpha–L–Aspartyl–L–Phenylalanine Alkyl Esters As Sweeteners", p. 535, AN 130 927v.

*Primary Examiner*—José G. Dees
*Assistant Examiner*—Samuel Barts
*Attorney, Agent, or Firm*—Oblon, Spivak, McClelland, Maier & Neustadt

[57] ABSTRACT

The methyl ester of α-L-aspartyl-L-phenylalanine may be obtained in high yields directly from a reaction solution which contains N-protected- or unprotected-α-L-aspartyl-D-phenylalanine (or its methyl ester derivative), and α-L-aspartyl-L-phenylalanine methyl ester by selective crystallization of the α-L-aspartyl-L-phenylalanine methyl ester hydrochloride from an aqueous solution containing N-protected- or unprotected-L-aspartyl-L-phenylalanine and/or its methyl ester derivative and N-protected- or unprotected-L-aspartyl-D-phenylalanine and/or its methyl ester derivative, hydrochloric acid, and methanol, with or without stirring.

12 Claims, No Drawings

METHOD FOR PRODUCTION OF α-L-ASPARTYL-L PHENYLALANINE METHYL ESTER HYDROCHLORIDE

BACKGROUND OF THE INVENTION

1. Field of the Invention

The present invention relates to a method for producing α-L-aspartyl-L-phenylalanine methyl ester hydrochloride (abbreviated as α-L-L-APM.HCl hereafter) by crystallizing α-L-aspartyl-L-phenylalanine methyl ester hydrochloride from an aqueous solution of L-aspartyl-L-phenylalanine and/or the methyl ester derivative thereof (including an N-protected type) and L-aspartyl-D-phenylalanine and/or the methyl ester derivative thereof (including an N-protected type) which contains hydrochloric acid and methanol, with or without stirring.

2. Discussion of the Background

α-L-L-APM is a low calorie sweetener of high quality, while α-L-aspartyl-D-phenylalanine methyl ester hydrochloride (abbreviated as α-L-D-APM.HCl hereafter) is tasteless and, thus, has no use as a sweetener. A variety of methods are known for the production of α-L-L-APM.

For example, hitherto known methods include: (a) the condensation of a N-protected-L-aspartic anhydride and the methyl ester of L-phenylalanine, followed by elimination of the N-protecting group according to a conventional method (U.S. Pat. No. 3,786,039); (b) the condensation of a N-protected-L-aspartic anhydride and L-phenylalanine, elimination of the N-protecting group according to a conventional method, followed by crystallization of α-L-L-APM.HCl in an aqueous solution of methanol (Japanese Unexamined Patent Publication SHO 49-41425); (c) the direct condensation of the methyl ester of L-phenylalanine with a strong acid addition salt of L-aspartic anhydride (Japanese Unexamined Patent Publication SHO 49-14217); (d) the condensation of a N-protected L-aspartic acid and the methyl ester of L-phenylalanine in the presence of an enzyme, followed by conventional elimination of the N-protecting group (Japanese Unexamined Patent Publication SHO 55-135595), etc.

The starting materials for these production methods are L-aspartic acid (abbreviated as L-Asp hereafter) and L-phenylalanine (abbreviated as L-Phe hereafter). L-Asp is easily produced by an enzymatic reaction of the substrates fumaric acid and ammonia and is available at a low cost. On the other hand, regarding L-Phe, although DL-phenylalanine (abbreviated as DL-Phe hereafter) may be synthesized cheaply, the cost for the requisite optical resolution is high, and the production of L-Phe by fermentation requires expensive purification for the removal of the by-products, resulting in a very costly method for producing α-L-L-APM.HCl, due to the use of the starting material, L-Phe. If DL-Phe were suitable for use in a method for producing of α-L-L-APM, then the method would be expected to be an advantageous one from an industrial viewpoint.

In this regard, production methods are already known which use L-Asp and DL-Phe as the starting materials. For example, a report has been made of a method where a N-protected-L-Asp and DL-Phe are condensed conventionally to produce N-Protected-α-L-aspartyl-L-phenylalanine (abbreviated as N-protected-α-L-L-AP hereafter) and N-protected-α-L-aspartyl-D-phenylalanine (abbreviated as N-protected-α-L-D-AP hereafter), after which the N-protected-α-L-L-AP is separated by crystallization (Japanese Unexamined Patent Publication SHO 63-445945), then the N-protecting group is eliminated in a conventional manner, thereby leading to α-L-L-APM. This production method, however, has a fatal drawback in that reliance on the difference in solubility between N-protected-α-L-L-AP and N-protected-α-L-D-AP prevents the obtaining of N-protected-α-L-L-AP in high yields.

Needless to say, the above drawback of the N-protected-AP cannot be overcome even if the N-protecting group is first eliminated from the N-protected-α-L-L-AP and N-protected-α-L-D-AP in the solution to yield a solution containing α-L-L-AP and α-L-D-AP, after which α-L-L-AP is subjected to conventional dissolution followed by cooling to crystallization. In other words, the isomers must be separated before removal of the N-protecting group, thus presenting industrial problems such as low yields and complicated operations for crystallization and separation.

Thus, there remains a need for a method for producing α-L-L-APM whereby a decrease in the yield of the desired α-L-L-APM due to the formation or presence of the byproduct L-D-AP (or its methyl ester derivative) is prevented and α-L-L-APM.HCl is crystallized directly from a reaction mixture which contains N-protected- or unprotected-L-D-AP (or its methyl ester derivative), selectively and in high yield, in the case where L-Phe containing DL-Phe and D-phenylalanine (abbreviated as D-Phe hereafter) is used as the starting material for production of the α-L-L-APM.

SUMMARY OF THE INVENTION

Accordingly, it is one object of the present invention to provide a novel method for the production of α-L-aspartyl-L-phenylalanine methyl ester hydrochloride (α-L-L-ADM.HCl).

It is another object of the present invention to provide a method for producing α-L-L-APM-HCl in high yield and high purity.

It is another object of the present invention to provide a method for producing α-L-L-APM.HCl which utilizes, as a starting material, phenylalanine which contains at least some DL-phenylalanine, DL-Phe.

It is another object of the present invention to provide a method for separating α-L-L-APM.HCl from a mixture which contains at least one of L-D-AP, L-D-APM, N-protected-L-D-AP, and N-protected-L-D-APM.

These and other objects, which will become apparent during the following detailed description have been achieved by the inventors' discovery that high yields of α-L-L-APM may be produced by selective crystallization of α-L-L-APM.HCl from a mixture containing L-L-AP and/or the methyl ester derivative thereof (including N-protected type) and L-D-AP and/or the methyl ester derivative thereof (including N-protected type) from an aqueous solution of hydrochloric acid and methanol, with or without stirring.

DETAILED DESCRIPTION OF THE PREFERRED EMBODIMENTS

For convenience the abbreviations used in the present specification are presented below in tabular form

| Compound | Abbreviation |
| --- | --- |
| α-L-aspartyl-L-phenylalanine methyl ester hydrochloride | α-L-L-APM.HCl |
| α-L-aspartyl-L-phenylalanine methyl ester | α-L-L-APM |
| α-L-aspartyl-L-phenylalanine | α-L-L-AP |
| α-L-aspartyl-D-phenylalanine methyl ester hydrochloride | α-L-D-APM.HCL |
| α-L-aspartyl-D-phenylalanine methyl ester | α-L-D-APM |
| α-L-aspartyl-D-phenylalanine | α-L-D-AP |
| L-aspartic acid | L-Asp |
| L-phenylalanine | L-Phe |
| DL-phenylalanine | DL-Phe |

Surprisingly, in the present invention L-D-AP, its methyl ester derivative and its hydrochloride are not crystallized from an aqueous solution of hydrochloric acid and methanol, and thus no trouble is encountered in the selective crystallization of α-L-L-APM.HCl in spite of the presence of a large quantity of these isomers. Owing to this discovery, now there is no need for prior removal of the unnecessary isomers.

The α-L-L-APM.HCl afforded by the present crystallization process may be converted into α-L-L-APM by any conventional known method, for example, neutralization with sodium carbonate in an aqueous solution, as described in Japanese unexamined patent publication Nos. SHO 63-145298 and HEI 3-221334, which are incorporated herein by reference. In addition, any phenylalanine remaining in the mother liquor of the crystallization of α-L-L-APM-HCl may be recovered from the mother liquor by any conventional known manner and may be used again after racemization, if necessary.

As mentioned above, use of L-Phe which contains DL-Phe and D-Phe as the starting material enables conversion of all the L-Phe into α-L-L-APM.

The N-protected-AP, AP, or its methyl ester derivative used according to the present invention may be obtained by any conventional known method for the production of α-L-L-APM, as described in Japanese unexamined patent publictaion No. SHO 51-113841, which is incorporated herein by reference.

In the context of the present invention, the N-protecting group may be a formyl group, a 1-$C_{1-4}$-alkyl-2-$C_{1-4}$-acyl-vinyl group, or any group which may be eliminated under acidic conditions according to the present invention. Preferably the N-protecting group is a formyl or a 1-methyl-2-acetyl-vinyl group. Suitable N-protecting groups are disclosed in Japanese unexamined patent publication No. SHO 55-35059, which is incorporated herein by reference.

Of course, it is to be understood that the methyl esters referred to in the present specification are those in which the carboxyl group of phenylalanine is esterified. Likewise, it should also be understood that the N-protected compounds referred to in the present specification are those in which the α-amino group of aspartic acid is protected.

The concentration of the N-protected-α-L-L-AP and its methyl ester derivative, the N-protecting group-eliminated version or α-L-L-AP and its methyl ester derivative in the crystallization solution may be suitably 0.1–2.5 M/l. The crystallization ratio of α-L-L-APM-HCl is poor at concentrations less than 0.1 M/l, whereas generally the viscosity of the solution tends to increase at concentrations greater than 0.5 M/l. A concentration of 0.2–2 M/l is preferred from a practical viewpoint.

There is no need to set limits on the concentrations of the α- or β-L-D-AP and their methyl ester derivatives in the crystallization solution; the original concentrations of the starting material will determine the amounts of these compounds in the crystallization solution. Typically, the concentration of the N-protected and/or N-unprotected α-L-D-AP and/or N-protected and/or N-unprotected α-L-D-APM will range from 2.5 M/l or less, more usually from 2.0 M/l or less. Typically, the concentration of the N-protected and/or N-unprotected β-L-D-AP and/or N-protected and/or N-unprotected β-L-D-APM will range from 0.6 M/l or less, more usually 0.5 M/l or less. Typically, the amounts of N-protected and/or N-unprotected α-L-D-AP and/or N-protected and/or N-unprotected α-L-D-APM [L-D-AP+L-D-APM] present in the crystallization solution relative to the amounts of N-protected and/or N-unprotected α-L-L-AP and/or N-protected and/or N-unprotected α-L-L-APM [L-L-AP+L-L-APM is 0.5 to 233% by weight of [L-D-AP+L-D-APM]/[L-L-AP+L-L-APM] or 0.5 to 70% by weight [L-D-AP+L-D-APM]/[L-D-AP+L-d-APM+L-L-AP+L-L-APM].

The acid used is hydrochloric acid, and also gaseous hydrogen chloride may be employed. The concentration of the acid may suitably be 0.5–6M/l in the crystallization solution. The crystallization rate of α-L-L-APM.HCl decreases at HCl concentrations less than 0.5 M/l, and a concentration of more than 6 M/l is not preferred, because of the occurrence of cleavage of the peptide. A practically preferred range of HCl concentration in the crystallization solution is 1–5 M/l.

The methanol concentration may suitably be 2.5 M/l or less. A concentration of more than 2.5 M/l is not preferred, because of an increase in the amount of the dimethyl ester of α-L-L-AP produced. A concentration of 2 M/l or less is desired from a practical viewpoint. The preferred concentration of methanol in the crystallization solution is 0.5 to 1.5 M/l.

The crystallization temperature range may suitably be −5° to 60° C. At temperatures less than −5° C. the crystallization rate of α-L-L-APM-HCl decreases, while temperatures greater than 60° C. are not preferred in view of the possibility of cleavage of the peptide. Practically, 5 to 45° C. is a desirable range.

The crystallization time varies depending on the type of the N-protecting group and the methyl ester derivative content of α-L-L-AP, but is normally 15 days or less. In actual practice, it is usually 10 days or less.

Needless to say, the ratio of the D- and L-forms in DL-Phe used as a starting material need not be 1:1. DL-Phe in the context of this invention includes all phenylalanine which contains at least some of the D-form. This DL-Phe may be employed in any conventional known method for production of the N-protected-AP and/or its methyl ester derivative or AP and/or its methyl ester derivative, all of which are suitable materials for the present crystallization method, as described in Japanese unexamined patent publication No. SHO 61-188341, which is incorporated herein by reference. The proportion of the D-form of Phe in the DL-Phe used as a starting material should be within a range of 0.5–70% by weight, preferably 0.5 to 60% by weight, based on the total weight of the DL-Phe. Most preferably, the DL-Phe utilized in the present process is nearly racemic and, thus, the proportion of the D-form of Phe in the DL-Phe is in the range of 40 to 60% by weight based on the total weight of the DL-Phe.

As described above, conventionally, those compounds in which the phenylalanine of aspartyl-phenylalanine is in the D-form must be separated prior to the crystallization of α-L-L-APM. But, the prior separation of the materials containing D-Phe has been made unnecessary by the present invention. Moreover, high yields of cheap α-L-L-APM can be now attained industrially, with drastically decreased energy consumption.

Other features of the invention will become apparent in the course of the following descriptions of exemplary embodiments which are given for illustration of the invention and are not intended to be limiting thereof.

EXAMPLES

Conditions for analysis with high performance liquid chromatography (abbreviated as HPLC hereafter) in the examples are as follows:

| Column: | Crown Pak CR (+) 4 mmφ × 150 mm |
|---|---|
| Mobile phase: | 10% aqueous solution of methanol (adjusted to pH 2.0 with perchloric acid) |
| Flow rate: | 0.7 ml/min. |
| Temperature: | room temperature |
| Detection wavelength: | 210 nm |

Example 1

To 10.0 g (34 mmol) of α-L-L-APM were added 10.0 g (34 mmol) of α-L-D-APM, 23 ml (260 mmol) of 35% hydrochloric acid, 0.5 ml (12 mmol) of methanol, and 25 ml of water, and the mixture was stirred at 20° C. for 1 day, followed by further stirring at 10° C. for 5 hours.

The precipitated crystals were separated by suction filtration, washed with 2N hydrochloric acid, and then dried to obtain 11.1 g of α-L-L-APM.HCl dihydrate. The results of analysis by HPLC showed the production of α-L-L-APM (yield: 80%), and neither α-L-D-AP nor its methyl ester derivative was detected in the crystallized product.

Example 2

To 9.5 g (34 mmol) of α-L-L-AP were added 5.2 g (17 mmol) of the dimethyl ester of α-L-D-AP, 17 ml (192 mmol) of 35% HCl, 2.6 ml (64 mmol) of methanol and 25 ml of water, and the mixture was stirred at 20° C. for 1 day, followed by further stirring at 10° C. for 3 hours.

The precipitated crystals were separated by suction filtration, washed with 2N hydrochloric acid, and then dried. Thus was produced 11.2 g of α-L-L-APM.HCl dihydrate. The results of analysis by HPLC showed that these crystals were α-L-L-APM (yield: 82%), and neither α-L-D-AP nor its methyl ester derivative was detected in the crystallized product.

Example 3

To 10.0 g (34 mmol) of α-L-L-AP which was methyl-esterified at the carboxyl group of the aspartic acid were added 2.5 g (8 mmol) of α-L-D-APM, 27 ml (306 mmol) of 35% HCl, 1.0 ml (25 mmol) of methanol, and 25 ml of water, and the mixture was stirred at 20° C. for 1 day and then at 5° C. for 4 hours.

The precipitated crystals were separated by suction filtration, washed with 2N hydrochloric acid, and then dried. Thus was produced 11.5 g of α-L-L-APM.HCl dihydrate. The results of analysis by HPLC showed that these crystals were α-L-L-APM (yield: 84%), and neither α-L-D-AP nor its methyl ester derivative was detected in the crystallized product.

Example 4

To 9.5 g (34 mmol) of α-L-L-AP were added 10.0 g (34 mmol) of α-L-D-APM, 1.9 g (7 mmol) of β-L-L-AP, 1.9 g (7 mmol) of β-L-D-AP, 32 ml (362 mmol) of 35% HCl, 4.9 ml (121 mmol) of methanol, and 35 ml of water, and the mixture was stirred at 20° C. for 2 days and then at 10° C. for 2 days. The precipitated crystals were separated by suction filtration, washed with 2N hydrochloric acid, and then dried. Thus was produced 11.2 g of α-L-L-APM.HCl dihydrate. The results of analysis by HPLC showed that these crystals were α-L-L-APM (yield: 81%), and neither L-D-AP nor its methyl ester derivative was detected in the crystallized product.

Example 5

To 10.0 g (34 mmol) of α-L-L-AP were added 2.5 g (8 mmol) of α-L-D-APM, 2.5 g (8 retool) of β-L-D-APM, 2.0 g (7 mmol) of β-L-L-APM, 0.1 g (1 mmol) of DL-Phe, 25 ml (283 mmol) of 35% HCl, 4.9 ml (121 mmol) of methanol, and 35 ml of water, and the mixture was stirred at 20° C. for 3 days and then at 5° C. for 1 day.

The precipitated crystals were separated by suction filtration, washed with 2N hydrochloric acid, and then dried. Thus was produced 11.2 g of α-L-L-APM.HCl dihydrate. The results of analysis by HPLC showed that these crystals were α-L-L-APM (yield: 81%), and neither L-D-AP nor its methyl ester derivative was detected in the crystallized product.

Example 6

To 11.0 g (34 mmol) of α-L-L-APM, the amino group of the aspartic acid of which is formylated, were added 11.0 g (34 mmol) of α-L-D-APM, the amino group of the aspartic acid of which is formylated, 2.5 g (8 mmol) of β-L-D-APM, 2.5 g (8 mmol) of β-L-L-APM, 28 ml (317 mmol) of 35% HCl, 5.3 ml (131 mmol) of methanol, and 35 ml of water, and the mixture was stirred at 20° C. for 5 days and then at 5° C. for 10 hours.

The precipitated crystals were separated by suction filtration, washed with 2N hydrochloric acid, and then dried. Thus was produced 11.3 g of α-L-L-APM.HCl dihydrate. The results of analysis by HPLC showed that these crystals were α-L-L-APM (yield: 82%), and neither L-D-AP nor its methyl ester derivative was detected in the crystallized product.

Example 7

In the presence of sulfuric acid, 6.6 g (40 mmol) of DL-Phe was heated with methanol, and the mixture was extracted with toluene to provide the methyl ester of DL-Phe extracted into toluene. The resulting solution in toluene was subjected to condensation with 5.8 g (41 mmol) of N-formyl-L-aspartic anhydride in the presence of acetic acid. The thus-obtained solution was subjected to a conventional post-treatment and then protected, followed addition of hydrochloric acid and methanol thereto to give final concentrations in the solution of 4N HCl and 1.5 M/l methanol. The mixture was subjected to crystallization at 20° C. for 5 days and at 10° C. for 1 day.

The precipitated crystals were separated by suction filtration, washed with 2N hydrochloric acid, and then dried. Thus was produced 5.8 g of α-L-L-APM-HCl dihydrate (yield: 71% to L-Phe). The results of analysis by HPLC showed that these crystals were α-L-L-APM, and neither L-D-AP nor its methyl ester derivative was detected in the crystallized product.

To an additional crop of α-L-L-APM.Hcl was added 90 ml of water, and the resulting mixture was adjusted to pH 4.8 with 15% aqueous solution of $Na_2CO_3$, followed by heating at 50° C. for dissolution, then the mixture was allowed to stand at 5° C. for 1 day. The precipitated crystals were separated by suction filtration, washed with cold water, and then dried. Thus was produced 2.9 g of α-L-L-APM (yield: 48% based on L-Phe). The results of analysis by HPLC showed that the product was α-L-L-APM, and neither L-D-AP nor its methyl ester derivative was detected in the product. This α-L-L-APM tasted favorably sweet.

Example 8

In the presence of sulfuric acid, 6.6 g (40mmol) of DL-Phe was added with methanol (1760 mmol) and heated. The mixture was neutralized with 15% $Na_2CO_3$ solution and extracted with toluene to obtain the methyl ester of DL-Phe. The concentration of the Phe methyl ester in the extracted solution was 10 g/dl. Then 68 ml of the resultant Phe methyl ester solution was condensed with 5.8 g (41 mmol) of N-formyl-L-aspartic anhydride in the presence of acetic acid. The major products in the reaction solution were N-formyl-α-L-L-APM (16mmol) and N-formyl-α-L-D-APM (16 mmol). The reaction solution was heated to remove acetic acid with distilling off toluene. The remaining toluene layer was subjected to extraction with water. Hydrochloric acid and methanol were added to the extracted aqueous layer to obtain final concentrations 4N for HCl and 1.5 M/l for methanol. The mixture was stirred at 20° C. for 10 days and at 10° C. for 3 days.

The precipitated crystals were separated by suction filtration and dried to obtain 5.7 g of α-L-L-APM.HCl dihydrate (yield: 72% to L-Phe). The analytical results by HPLC showed that the product was α-L-L-APM and neither L-D-AP nor its methyl ester was detected in the crystallized product. This α-L-L-APM tasted favorably sweet.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for producing α-L-aspartyl-L-phenylalanine methyl ester hydrochloride, comprising:
    selectively crystallizing α-L-aspartyl-L-phenylalanine methyl ester hydrochloride from an aqueous solution comprising (a) hydrochloric acid; (b) methanol; (c) at least one compound selected from the group consisting of N-protected-α-L-aspartyl-L-phenylalanine, α-L-aspartyl-L-phenylalanine, N-protected-α-L-aspartyl-L-phenylalanine methyl ester, and α-L-aspartyl-L-phenylalanine methyl ester; and (d) at least one compound selected from the group consisting of N-protected-α-L-aspartyl-D-phenylalanine, α-L-aspartyl-D-phenylalanine, N-protected-α-L-aspartyl-D-phenylalanine methyl ester, and α-L-aspartyl-D-phenylalanine methyl ester, with or without stirring, to obtain crystallized α-L-aspartyl-L-phenylalanine methyl ester hydrochloride.

2. The method of claim 1, wherein the N-protecting group in said N-protected-α-L-aspartyl-L-phenylalanine, said N-protected-α-L-aspartyl-L-phenylalanine methyl ester, said N-protected-α-L-aspartyl-D-phenylalanine and said N-protected-α-L-aspartyl-D-phenylalanine methyl ester is a formyl group or a 1-$C_{1-4}$-alkyl-2-$C_{1-4}$-acyl-vinyl group.

3. The method of claim 1, wherein the proportion of said (d) at least one compound selected from the group consisting of N-protected-α-L-aspartyl-D-phenylalanine, α-L-aspartyl-D-phenylalanine, N-protected-α-L-aspartyl-D-phenylalanine methyl ester, and α-L-aspartyl-D-phenylalanine methyl ester is in the range 0.5 to 233% by weight based on the total weight of said (c) at least one compound selected from the group consisting of N-protected-α-L-aspartyl-L-phenylalanine, α-L-aspartyl-L-phenylalanine, N-protected-α-L-aspartyl-L-phenylalanine methyl ester, and α-L-aspartyl-L-phenylalanine methyl ester.

4. A method for producing α-L-aspartyl-L-phenylalanine methyl ester hydrochloride, comprising:
    (i) condensing (a) one member selected from the group consisting of DL-phenylalanine, the methyl ester of DL-phenylalanine, and mixtures thereof with (b) N-protected-aspartic anhydride, to obtain a mixture comprising (i) N-protected-α-L-aspartyl-L-phenylalanine methyl ester and N-protected-α-L-aspartyl-D-phenylalanine methyl ester, or (ii) N-protected-α-L-aspartyl-L-phenylalanine and N-protected-α-L-aspartyl-D-phenylalanine;
    (ii) forming an aqueous crystallization solution comprising (a') said mixture comprising said (i) N-protected-α-L-aspartyl-L-phenylalanine methyl ester and N-protected-α-L-aspartyl-D-phenylalanine methyl ester, or said (ii) N-protected-α-L-aspartyl-L-phenylalanine and N-protected-α-L-aspartyl-D-phenylalanine; (b') hydrochloric acid; and (c') methanol; and
    (iii) selectively crystallizing α-L-aspartyl-L-phenylalanine methyl ester hydrochloride from said crystallization solution.

5. The method of claim 4, wherein the N-protecting group in said N-protected-aspartic anhydride is a formyl group or a 1-$C_{1-4}$-alkyl-2-$C_{1-4}$-acyl-vinyl group.

6. The method of claim 4, wherein the total amount of said N-protected-α-L-aspartyl-D-phenylalanine and said N-protected-α-L-aspartyl-D-phenylalanine methyl ester present in said crystallization solution is 0.5 to 233 wt % based on the total amount of said N-protected-α-L-aspartyl-L-phenylalanine and said N-protected-α-L-aspartyl-L-phenylalanine methyl ester present in said crystallization solution.

7. In a method for producing α-L-aspartyl-L-phenylalanine methyl ester hydrochloride, comprising condensing (a) a member selected from the group consisting of DL-phenylalanine, the methyl ester of DL-phenylalanine, and mixtures thereof with (b) N-protected-aspartic anhydride, to obtain a mixture comprising (i) N-protected-α-L-aspartyl-L-phenylalanine methyl ester and N-protected-L-aspartyl-D-phenylalanine methyl ester, or (ii) N-protected-L-aspartyl-L-phenylalanine and N-protected-L-aspartyl-D-phenylalanine, the improvement being selectively crystallizing said α-L-aspartyl-L-phenylalanine methyl ester hydrochloride from an aqueous crystallization solution comprising (a') said mixture comprising (i) N-protected-α-L-aspartyl-L-phenylalanine methyl ester and N-protected-L-aspartyl-D-phenylalanine methyl ester, or (ii) N-protected-L-aspartyl-L-phenylalanine and N-protected-L-aspartyl-D-phenylalanine, (b') hydrochloric acid, and (c') methanol, to obtain crystallized α-L-aspartyl-L-phenylalanine methyl ester hydrochloride.

8. The method of claim 7, wherein the N-protecting group in said N-protected-aspartic anhydride is a formyl group or a 1-$C_{1\text{-}4}$-alkyl-2-$C_{1\text{-}4}$-acyl-vinyl group.

9. The method of claim 7, wherein the total amount of said N-protected-α-L-aspartyl-D-phenylalanine and said N-protected-α-L-aspartyl-D-phenylalanine methyl ester present in said crystallization solution is 0.5 to 233 wt % based on the total amount of said N-protected-α-L-aspartyl-L-phenylalanine and said N-protected-α-L-aspartyl-L-phenylalanine methyl ester present in said crystallization solution.

10. A method of separating α-L-aspartyl-L-phenylalanine methyl ester hydrochloride from a mixture, comprising:

selectively crystallizing α-L-aspartyl-L-phenylalanine methyl ester hydrochloride from an aqueous mixture comprising:

(a) at least one compound selected from the group consisting of N-protected-α-L-aspartyl-L-phenylalanine methyl ester, α-L-aspartyl-L-phenylalanine methyl ester, N-protected-α-L-aspartyl-L-phenylalanine, and α-L-aspartyl-L-phenylalanine;

(b) at least one compound selected from the group consisting of N-protected-α-L-aspartyl-D-phenylalanine methyl ester, α-L-aspartyl-D-phenylalanine methyl ester, N-protected-α-L-aspartyl-D-phenylalanine, and α-L-aspartyl-D-phenylalanine;

(c) hydrochloric acid; and (d) methanol, to obtain crystallized α-L-aspartyl-L-phenylalanine methyl ester hydrochloride.

11. The method of claim 10, wherein the N-protecting group in said N-protected-α-L-aspartyl-L-phenylalanine methyl ester, said N-protected-α-L-aspartyl-L-phenylalanine, said N-protected-α-L-aspartyl-D-phenylalanine methyl ester, and said N-protected-α-L-aspartyl-D-phenylalanine is a formyl group or a 1-$C_{1\text{-}4}$-alkyl-2-$C_{1\text{-}4}$-acyl-vinyl group.

12. The method of claim 10, wherein the proportion of said (b) at least one compound selected from the group consisting of N-protected-α-L-aspartyl-D-phenylalanine methyl ester, α-L-aspartyl-D-phenylalanine methyl ester, N-protected-α-L-aspartyl-D-phenylalanine, and α-L-aspartyl-D-phenylalanine, in said mixture is within a range of 0.5 to 233% by weight, based on the total weight of said (a) at least one compound selected from the group consisting of N-protected-α-L-aspartyl-L-phenylalanine methyl ester, α-L-aspartyl-L-phenylalanine methyl ester, N-protected-α-L-aspartyl-L-phenylalanine, and α-L-aspartyl-L-phenylalanine.

* * * * *

UNITED STATES PATENT AND TRADEMARK OFFICE
CERTIFICATE OF CORRECTION

PATENT NO. : 5,371,269
DATED     : December 6, 1994
INVENTOR(S) : Kazutaka NAGASHIMA, et al.

It is certified that error appears in the above-indentified patent and that said Letters Patent is hereby corrected as shown below:

On the title page, Item[30], the Foreign Application Priority Numbers are listed incorrectly. They should read:

--4-170654 and 4-180837--

Signed and Sealed this

Twenty-eight Day of March, 1995

Attest:

BRUCE LEHMAN

Attesting Officer

Commissioner of Patents and Trademarks